US012699090B2

(12) United States Patent
Kapur et al.

(10) Patent No.: US 12,699,090 B2
(45) Date of Patent: Aug. 4, 2026

(54) DIAGNOSTIC REAGENTS

(71) Applicants: The Penn State Research Foundation, State College, PA (US); The Secretary of State for Environment, Food and Rural Affairs acting through the Animal and Plant Health Agency, Surrey (GB)

(72) Inventors: Vivek Kapur, State College, PA (US); Sreenidhi Srinivasan, State College, PA (US); Hans Vordermeier, Surrey (GB); Gareth Jones, Surrey (GB)

(73) Assignees: The Penn State Research Foundation, State College, PA (US); The Secretary of State for Environment, Food and Rural Affairs acting through the Animal and Plant, Surrey (GB)

( * ) Notice: Subject to any disclaimer, the term of this patent is extended or adjusted under 35 U.S.C. 154(b) by 1065 days.

(21) Appl. No.: 17/602,628

(22) PCT Filed: Apr. 9, 2020

(86) PCT No.: PCT/GB2020/050936
§ 371 (c)(1),
(2) Date: Oct. 8, 2021

(87) PCT Pub. No.: WO2020/208368
PCT Pub. Date: Oct. 15, 2020

(65) Prior Publication Data
US 2022/0196656 A1 Jun. 23, 2022

Related U.S. Application Data

(60) Provisional application No. 62/832,034, filed on Apr. 10, 2019.

(30) Foreign Application Priority Data

May 2, 2019 (GB) ..................................... 1906193

(51) Int. Cl.
*G01N 33/569* (2006.01)
*C07K 14/35* (2006.01)

(52) U.S. Cl.
CPC ......... *G01N 33/5695* (2013.01); *C07K 14/35* (2013.01)

(58) Field of Classification Search
None
See application file for complete search history.

(56) References Cited

FOREIGN PATENT DOCUMENTS

| CN | 102608333 A | 7/2012 |
| WO | 2011135369 A1 | 11/2011 |
| WO | 2015090322 A1 | 6/2015 |

OTHER PUBLICATIONS

Greenspan et al. Nature Biotechnology 17: 936-937, 1999.*
Skolnick et al. Trends in Biotechnology, 18: 34-39, 2000.*
Rudinger J. In: Peptide Hormones. (Ed) JA Parsons, University Park Press, pp. 1-7, 1976.*
Lazar et al. Mol. Cellular Biol. 8: 1247-1252, 1988.*
McGuinness et al. Lancet 337: 514-517, 1991.*
McGuinness et al. Mol. Microbiol. 7: 505-514, 1993.*
Pajon et al. Infect. Immun. 80: 2667-2677, 2012.*
Shuguang et al., "CTL immunogenicity of Rv3615c Antigen and Diagnostic Performances of an Esat-6/cfp-10/rv3615c Antigen Cocktail Formycobacterium Tuberculosisinfection", Tuberculosis, vol. 107, pp. 5-12, Dec. 2017.
Whelan et al., "Development of a Skin Test for Bovine Tuberculosis for Differentiating Infected From Vaccinated Animals", Journal of Clinical Microbiology, vol. 48, No. 9, pp. 3176-3181, Sep. 1, 2010.
International Search Report and Written Opinion received in International Application No. PCT/GB2020/050936, mailed on Jun. 26, 2020, 19 pages.

* cited by examiner

*Primary Examiner* — S. Devi
(74) *Attorney, Agent, or Firm* — Howson & Howson LLP; Colleen M. Schaller

(57) ABSTRACT

There is provided a skin test diagnostic reagent comprising: at least one 40mer polypeptide consisting of any one of SEQ ID NOs: 1, 3 or 4; at least one 40mer polypeptide consisting of any one of SEQ ID NOs: 7 or 8; and at least one 40mer polypeptide consisting of any one of SEQ ID NOs: 10, 11 or 12, characterised in that the reagent elicits a positive result when administered in a skin test to an animal infected with *Mycobacterium bovis* or *Mycobacterium tuberculosis*.

11 Claims, 6 Drawing Sheets

Specification includes a Sequence Listing.

| Antigen | Positive | Negative | Sensitivity |
|---|---|---|---|
| PPD-B | 22 | 3 | 88% (75, 100) |
| PCL | 19 | 6 | 76% (59, 93) |
| PC-1 | 17 | 8 | 68% (50, 86) |
| PPD(B-A) | 12 | 13 | 48% (28, 68) |
| PPD(B-A) severe interpretation | 19 | 6 | 76% (59, 93) |

SEQUENCE LISTING

```
<160> NUMBER OF SEQ ID NOS: 44

<210> SEQ ID NO 1
<211> LENGTH: 40
<212> TYPE: PRT
<213> ORGANISM: Artificial Sequence
<220> FEATURE:
<223> OTHER INFORMATION: synthetic protein fragment

<400> SEQUENCE: 1

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala
        35                  40

<210> SEQ ID NO 2
<211> LENGTH: 40
<212> TYPE: PRT
<213> ORGANISM: Artificial Sequence
<220> FEATURE:
<223> OTHER INFORMATION: synthetic protein fragment

<400> SEQUENCE: 2

Asn Val Thr Ser Ile His Ser Leu Leu Asp Glu Gly Lys Gln Ser Leu
1               5                   10                  15
```

```
Thr Lys Leu Ala Ala Ala Trp Gly Gly Ser Gly Ser Glu Ala Tyr Gln
            20                  25                  30

Gly Val Gln Gln Lys Trp Asp Ala
        35                  40

<210> SEQ ID NO 3
<211> LENGTH: 40
<212> TYPE: PRT
<213> ORGANISM: Artificial Sequence
<220> FEATURE:
<223> OTHER INFORMATION: artificial protein fragment

<400> SEQUENCE: 3

Ala Ala Trp Gly Gly Ser Gly Ser Glu Ala Tyr Gln Gly Val Gln Gln
1               5                   10                  15

Lys Trp Asp Ala Thr Ala Thr Glu Leu Asn Asn Ala Leu Gln Asn Leu
            20                  25                  30

Ala Arg Thr Ile Ser Glu Ala Gly
        35                  40

<210> SEQ ID NO 4
<211> LENGTH: 35
<212> TYPE: PRT
<213> ORGANISM: Artificial Sequence
<220> FEATURE:
<223> OTHER INFORMATION: artificial protein fragment

<400> SEQUENCE: 4

Thr Ala Thr Glu Leu Asn Asn Ala Leu Gln Asn Leu Ala Arg Thr Ile
1               5                   10                  15

Ser Glu Ala Gly Gln Ala Met Ala Ser Thr Glu Gly Asn Val Thr Gly
            20                  25                  30

Met Phe Ala
        35

<210> SEQ ID NO 5
<211> LENGTH: 40
<212> TYPE: PRT
<213> ORGANISM: Artificial Sequence
<220> FEATURE:
<223> OTHER INFORMATION: artificial protein fragment

<400> SEQUENCE: 5

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln
        35                  40

<210> SEQ ID NO 6
<211> LENGTH: 40
<212> TYPE: PRT
<213> ORGANISM: Artificial Sequence
<220> FEATURE:
<223> OTHER INFORMATION: artificial protein fragment

<400> SEQUENCE: 6

Ile Ser Gly Asp Leu Lys Thr Gln Ile Asp Gln Val Glu Ser Thr Ala
1               5                   10                  15

Gly Ser Leu Gln Gly Gln Trp Arg Gly Ala Ala Gly Thr Ala Ala Gln
            20                  25                  30
```

Ala Ala Val Val Arg Phe Gln Glu
        35                  40

<210> SEQ ID NO 7
<211> LENGTH: 40
<212> TYPE: PRT
<213> ORGANISM: Artificial Sequence
<220> FEATURE:
<223> OTHER INFORMATION: artificial protein fragment

<400> SEQUENCE: 7

Gly Gln Trp Arg Gly Ala Ala Gly Thr Ala Ala Gln Ala Ala Val Val
1               5                  10                  15

Arg Phe Gln Glu Ala Ala Asn Lys Gln Lys Gln Glu Leu Asp Glu Ile
            20                  25                  30

Ser Thr Asn Ile Arg Gln Ala Gly
        35                  40

<210> SEQ ID NO 8
<211> LENGTH: 40
<212> TYPE: PRT
<213> ORGANISM: Artificial Sequence
<220> FEATURE:
<223> OTHER INFORMATION: artificial protein fragment

<400> SEQUENCE: 8

Ala Ala Asn Lys Gln Lys Gln Glu Leu Asp Glu Ile Ser Thr Asn Ile
1               5                  10                  15

Arg Gln Ala Gly Val Gln Tyr Ser Arg Ala Asp Glu Glu Gln Gln Gln
            20                  25                  30

Ala Leu Ser Ser Gln Met Gly Phe
        35                  40

<210> SEQ ID NO 9
<211> LENGTH: 40
<212> TYPE: PRT
<213> ORGANISM: Artificial Sequence
<220> FEATURE:
<223> OTHER INFORMATION: artificial protein fragment

<400> SEQUENCE: 9

Met Thr Glu Asn Leu Thr Val Gln Pro Glu Arg Leu Gly Val Leu Ala
1               5                  10                  15

Ser His His Asp Asn Ala Ala Val Asp Ala Ser Ser Gly Val Glu Ala
            20                  25                  30

Ala Ala Gly Leu Gly Glu Ser Val
        35                  40

<210> SEQ ID NO 10
<211> LENGTH: 40
<212> TYPE: PRT
<213> ORGANISM: Artificial Sequence
<220> FEATURE:
<223> OTHER INFORMATION: artificial protein fragment

<400> SEQUENCE: 10

Ala Ile Thr His Gly Pro Tyr Cys Ser Gln Phe Asn Asp Thr Leu Asn
1               5                  10                  15

Val Tyr Leu Thr Ala His Asn Ala Leu Gly Ser Ser Leu His Thr Ala
            20                  25                  30

Gly Val Asp Leu Ala Lys Ser Leu
        35                  40

```
<210> SEQ ID NO 11
<211> LENGTH: 40
<212> TYPE: PRT
<213> ORGANISM: Artificial Sequence
<220> FEATURE:
<223> OTHER INFORMATION: artificial protein fragment

<400> SEQUENCE: 11

Ala His Asn Ala Leu Gly Ser Ser Leu His Thr Ala Gly Val Asp Leu
1               5                   10                  15

Ala Lys Ser Leu Arg Ile Ala Ala Lys Ile Tyr Ser Glu Ala Asp Glu
            20                  25                  30

Ala Trp Arg Lys Ala Ile Asp Gly
        35                  40

<210> SEQ ID NO 12
<211> LENGTH: 23
<212> TYPE: PRT
<213> ORGANISM: Artificial Sequence
<220> FEATURE:
<223> OTHER INFORMATION: artificial protein fragment

<400> SEQUENCE: 12

Arg Ile Ala Ala Lys Ile Tyr Ser Glu Ala Asp Glu Ala Trp Arg Lys
1               5                   10                  15

Ala Ile Asp Gly Leu Phe Thr
            20

<210> SEQ ID NO 13
<211> LENGTH: 16
<212> TYPE: PRT
<213> ORGANISM: Artificial Sequence
<220> FEATURE:
<223> OTHER INFORMATION: artificial protein fragment

<400> SEQUENCE: 13

Met Thr Glu Gln Gln Trp Asn Phe Ala Gly Ile Glu Ala Ala Ala Ser
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: artificial protein fragment

<400> SEQUENCE: 14

Ala Gly Ile Glu Ala Ala Ala Ser Ala Ile Gln Gly Asn Val Thr Ser
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: artificial protein fragment

<400> SEQUENCE: 15

Ala Ile Gln Gly Asn Val Thr Ser Ile His Ser Leu Leu Asp Glu Gly
1               5                   10                  15

<210> SEQ ID NO 16
<211> LENGTH: 16
<212> TYPE: PRT
```

```
<213> ORGANISM: Artificial Sequence
<220> FEATURE:
<223> OTHER INFORMATION: artificial protein fragment

<400> SEQUENCE: 16

Ile His Ser Leu Leu Asp Glu Gly Lys Gln Ser Leu Thr Lys Leu Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: artificial protein fragment

<400> SEQUENCE: 17

Lys Gln Ser Leu Thr Lys Leu Ala Ala Ala Trp Gly Gly Ser Gly Ser
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: artificial protein fragment

<400> SEQUENCE: 18

Ala Ala Trp Gly Gly Ser Gly Ser Glu Ala Tyr Gln Gly Val Gln Gln
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: artificial protein fragment

<400> SEQUENCE: 19

Glu Ala Tyr Gln Gly Val Gln Gln Lys Trp Asp Ala Thr Ala Thr Glu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: artificial protein fragment

<400> SEQUENCE: 20

Lys Trp Asp Ala Thr Ala Thr Glu Leu Asn Asn Ala Leu Gln Asn Leu
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: artificial protein fragment

<400> SEQUENCE: 21

Leu Asn Asn Ala Leu Gln Asn Leu Ala Arg Thr Ile Ser Glu Ala Gly
1               5                   10                  15

<210> SEQ ID NO 22
<211> LENGTH: 16
<212> TYPE: PRT
<213> ORGANISM: Artificial Sequence
```

-continued

```
<220> FEATURE:
<223> OTHER INFORMATION: artificial protein fragment

<400> SEQUENCE: 22

Ala Arg Thr Ile Ser Glu Ala Gly Gln Ala Met Ala Ser Thr Glu Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: artificial protein fragment

<400> SEQUENCE: 23

Gln Ala Met Ala Ser Thr Glu Gly Asn Val Thr Gly Met Phe Ala
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: artificial protein fragment

<400> SEQUENCE: 24

Met Ala Glu Met Lys Thr Asp Ala Ala Thr Leu Ala Gln Glu Ala Gly
1               5                   10                  15

Asn Phe

<210> SEQ ID NO 25
<211> LENGTH: 16
<212> TYPE: PRT
<213> ORGANISM: Artificial Sequence
<220> FEATURE:
<223> OTHER INFORMATION: artificial protein fragment

<400> SEQUENCE: 25

Gln Glu Ala Gly Asn Phe Glu Arg Ile Ser Gly Asp Leu Lys Thr Gln
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: artificial protein fragment

<400> SEQUENCE: 26

Glu Arg Ile Ser Gly Asp Leu Lys Thr Gln Ile Asp Gln Val Glu Ser
1               5                   10                  15

Thr Ala

<210> SEQ ID NO 27
<211> LENGTH: 17
<212> TYPE: PRT
<213> ORGANISM: Artificial Sequence
<220> FEATURE:
<223> OTHER INFORMATION: artificial protein fragment

<400> SEQUENCE: 27

Ile Asp Gln Val Glu Ser Thr Ala Gly Ser Leu Gln Gly Gln Trp Arg
1               5                   10                  15

Gly
```

-continued

```
<210> SEQ ID NO 28
<211> LENGTH: 18
<212> TYPE: PRT
<213> ORGANISM: Artificial Sequence
<220> FEATURE:
<223> OTHER INFORMATION: artificial protein fragment

<400> SEQUENCE: 28

Gly Ser Leu Gln Gly Gln Trp Arg Gly Ala Ala Gly Thr Ala Ala Gln
1               5                   10                  15

Ala Ala

<210> SEQ ID NO 29
<211> LENGTH: 18
<212> TYPE: PRT
<213> ORGANISM: Artificial Sequence
<220> FEATURE:
<223> OTHER INFORMATION: artificial protein fragment

<400> SEQUENCE: 29

Ala Gly Thr Ala Ala Gln Ala Ala Val Val Arg Phe Gln Glu Ala Ala
1               5                   10                  15

Asn Lys

<210> SEQ ID NO 30
<211> LENGTH: 18
<212> TYPE: PRT
<213> ORGANISM: Artificial Sequence
<220> FEATURE:
<223> OTHER INFORMATION: artificial protein fragment

<400> SEQUENCE: 30

Val Val Arg Phe Gln Glu Ala Ala Asn Lys Gln Lys Gln Glu Leu Asp
1               5                   10                  15

Glu Ile

<210> SEQ ID NO 31
<211> LENGTH: 20
<212> TYPE: PRT
<213> ORGANISM: Artificial Sequence
<220> FEATURE:
<223> OTHER INFORMATION: artificial protein fragment

<400> SEQUENCE: 31

Gln Lys Gln Glu Leu Asp Glu Ile Ser Thr Asn Ile Arg Gln Ala Gly
1               5                   10                  15

Val Gln Tyr Ser
            20

<210> SEQ ID NO 32
<211> LENGTH: 18
<212> TYPE: PRT
<213> ORGANISM: Artificial Sequence
<220> FEATURE:
<223> OTHER INFORMATION: artificial protein fragment

<400> SEQUENCE: 32

Asn Ile Arg Gln Ala Gly Val Gln Tyr Ser Arg Ala Asp Glu Glu Gln
1               5                   10                  15

Gln Gln

<210> SEQ ID NO 33
<211> LENGTH: 16
```

```
<212> TYPE: PRT
<213> ORGANISM: Artificial Sequence
<220> FEATURE:
<223> OTHER INFORMATION: artificial protein fragment

<400> SEQUENCE: 33

Arg Ala Asp Glu Glu Gln Gln Gln Ala Leu Ser Ser Gln Met Gly Phe
1               5                   10                  15

<210> SEQ ID NO 34
<211> LENGTH: 20
<212> TYPE: PRT
<213> ORGANISM: Artificial Sequence
<220> FEATURE:
<223> OTHER INFORMATION: artificial protein fragment

<400> SEQUENCE: 34

Met Thr Glu Asn Leu Thr Val Gln Pro Glu Arg Leu Gly Val Leu Ala
1               5                   10                  15

Ser His His Asp
            20

<210> SEQ ID NO 35
<211> LENGTH: 20
<212> TYPE: PRT
<213> ORGANISM: Artificial Sequence
<220> FEATURE:
<223> OTHER INFORMATION: artificial protein fragment

<400> SEQUENCE: 35

Pro Glu Arg Leu Gly Val Leu Ala Ser His His Asp Asn Ala Ala Val
1               5                   10                  15

Asp Ala Ser Ser
            20

<210> SEQ ID NO 36
<211> LENGTH: 20
<212> TYPE: PRT
<213> ORGANISM: Artificial Sequence
<220> FEATURE:
<223> OTHER INFORMATION: artificial protein fragment

<400> SEQUENCE: 36

Ser His His Asp Asn Ala Ala Val Asp Ala Ser Ser Gly Val Glu Ala
1               5                   10                  15

Ala Ala Gly Leu
            20

<210> SEQ ID NO 37
<211> LENGTH: 20
<212> TYPE: PRT
<213> ORGANISM: Artificial Sequence
<220> FEATURE:
<223> OTHER INFORMATION: artificial protein fragment

<400> SEQUENCE: 37

Asp Ala Ser Ser Gly Val Glu Ala Ala Ala Gly Leu Gly Glu Ser Val
1               5                   10                  15

Ala Ile Thr His
            20

<210> SEQ ID NO 38
<211> LENGTH: 20
<212> TYPE: PRT
<213> ORGANISM: Artificial Sequence
```

<220> FEATURE:
<223> OTHER INFORMATION: artificial protein fragment

<400> SEQUENCE: 38

Ala Ala Gly Leu Gly Glu Ser Val Ala Ile Thr His Gly Pro Tyr Cys
1               5                   10                  15

Ser Gln Phe Asn
            20

<210> SEQ ID NO 39
<211> LENGTH: 20
<212> TYPE: PRT
<213> ORGANISM: Artificial Sequence
<220> FEATURE:
<223> OTHER INFORMATION: artificial protein fragment

<400> SEQUENCE: 39

Ala Ile Thr His Gly Pro Tyr Cys Ser Gln Phe Asn Asp Thr Leu Asn
1               5                   10                  15

Val Tyr Leu Thr
            20

<210> SEQ ID NO 40
<211> LENGTH: 20
<212> TYPE: PRT
<213> ORGANISM: Artificial Sequence
<220> FEATURE:
<223> OTHER INFORMATION: artificial protein fragment

<400> SEQUENCE: 40

Ser Gln Phe Asn Asp Thr Leu Asn Val Tyr Leu Thr Ala His Asn Ala
1               5                   10                  15

Leu Gly Ser Ser
            20

<210> SEQ ID NO 41
<211> LENGTH: 20
<212> TYPE: PRT
<213> ORGANISM: Artificial Sequence
<220> FEATURE:
<223> OTHER INFORMATION: artificial protein fragment

<400> SEQUENCE: 41

Val Tyr Leu Thr Ala His Asn Ala Leu Gly Ser Ser Leu His Thr Ala
1               5                   10                  15

Gly Val Asp Leu
            20

<210> SEQ ID NO 42
<211> LENGTH: 20
<212> TYPE: PRT
<213> ORGANISM: Artificial Sequence
<220> FEATURE:
<223> OTHER INFORMATION: artificial protein fragment

<400> SEQUENCE: 42

Leu Gly Ser Ser Leu His Thr Ala Gly Val Asp Leu Ala Lys Ser Leu
1               5                   10                  15

Arg Ile Ala Ala
            20

<210> SEQ ID NO 43
<211> LENGTH: 20
<212> TYPE: PRT

-continued

```
<213> ORGANISM: Artificial Sequence
<220> FEATURE:
<223> OTHER INFORMATION: artificial protein fragment

<400> SEQUENCE: 43

Gly Val Asp Leu Ala Lys Ser Leu Arg Ile Ala Ala Lys Ile Tyr Ser
1               5                   10                  15

Glu Ala Asp Glu
            20

<210> SEQ ID NO 44
<211> LENGTH: 20
<212> TYPE: PRT
<213> ORGANISM: Artificial Sequence
<220> FEATURE:
<223> OTHER INFORMATION: artificial protein fragment

<400> SEQUENCE: 44

Arg Ile Ala Ala Lys Ile Tyr Ser Glu Ala Asp Glu Ala Trp Arg Lys
1               5                   10                  15

Ala Ile Asp Gly
            20
```

DIAGNOSTIC REAGENTS

CROSS-REFERENCE TO RELATED APPLICATIONS

This application is a national phase filing under 35 U.S.C. § 371 of International Application No. PCT/GB2020/050936 filed Apr. 9, 2020, which claims benefit under 35 U.S.C. § 119 (e) of U.S. Provisional Application No. 62/832,034 filed on 10 Apr. 2019, the contents of which are incorporated herein by reference in their entirety.

This invention was made with United States Government support under Hatch Act Project No. PEN04637 awarded by the United States Department of Agriculture. The United States Government has certain rights in the invention

TECHNICAL FIELD

This invention relates to reagents for use in a skin test for detection of *mycobacterium* infections, particularly *Mycobacterium tuberculosis* and *M. bovis*, in mammals such as cattle.

BACKGROUND

Tuberculosis, caused by *Mycobacterium tuberculosis* var *tuberculosis*, is one of the world's deadliest infectious diseases, claiming as many as three human lives every minute (1-3). The closely related *Mycobacterium tuberculosis* var *bovis* (*M. bovis*), is the main cause of *tuberculosis* in a wide variety of animal hosts including cattle (bovine TB or bTB), and significantly limits livestock productivity (4-7). Importantly, bTB represents a serious zoonotic threat, and is estimated to cause approximately 10% of the total human TB cases worldwide (8-10). While bTB is well controlled in most high-income countries through the implementation of strict test and cull strategies, the disease remains endemic in most low- and middle-income countries where national control programs have not yet been implemented for socio-economic reasons, and hence continues to contribute major losses to animal productivity along with human morbidity and mortality (11-14).

Based on an approach initially established more than a century ago, the current standard for diagnosis of bTB in animals works by measuring cell-mediated immune response following an intradermal skin test with the poorly defined and highly variable tuberculin skin test (TST) antigen (15, 16). More recently, an in vitro interferon-γ release assay (IGRA) has been introduced as an ancillary test in order to improve the overall sensitivity of detection of bTB-infected animals (17, 18). The poorly standardized stimulating antigens in the TST ("purified protein derivative" or PPD) are extracts obtained from the heat-killed cultures of specified strains of mycobacteria grown on glycerol broth (19, 20). For instance, bovine PPD (PPD-B) is derived from an extract of *M. bovis* AN5 strain culture, while avian PPD (PPD-A) is a similarly prepared extract from *M. avium* subsp. *avium* D4ER (21). In regions with high exposure to environmental mycobacteria, the difference in increase in skin induration reaction between bovine and avian PPD (i.e. PPD B-A) is ascertained using the single intradermal comparative cervical tuberculin test (SICCT) to improve test specificity, but this is also known to reduce assay sensitivity (15).

Furthermore, in addition to the poor standardization of the PPDs, the presence of cross-reactive antigens between the pathogenic and vaccine strains in the crude whole cell antigen preparation renders the PPD-based TST unable to differentiate infected from bacille Calmette-Guérin (BCG) vaccinated animals, thereby limiting opportunities for the development of BCG vaccination-based control programs (22-25).

Hence, there is a well-recognized and urgent need to develop defined antigen based bTB diagnostic assays with the ability to 'differentiate infected from vaccinated animals' (i.e. "DIVA" assays) for use alongside future (vaccination-based) control programs in regions where conventional test and cull strategies are not feasible for socio-economic reasons (26).

Over the past two decades, comparative genomic and transcriptome analyses have identified several specific *M. bovis* antigens with DIVA capability, including ESAT-6, CFP-10 and Rv3615c, that are present in field strains of *M. bovis* but are either absent or not immunogenic in the widely used vaccine strain, BCG (27, 28). When used in combination, these antigens have shown promise in both detecting infected animals as well as differentiating them from those vaccinated with BCG (29).

There remains, however, a need to develop an improved skin test antigen with DIVA capability that might serve as a reliable, easy to produce and fit-for-purpose assay for diagnosis of bTB.

SUMMARY OF THE INVENTION

Through extensive investigations, the inventors have provided polypeptide fragment skin test diagnostic reagents that provide unexpectedly good results when used in a skin test for bovine *tuberculosis*. Not only do these reagents have equal or superior performance characteristics over the extant standard tuberculin surveillance tests, but many of the limitations of the current assays have been obviated. This enables the development and implementation of critically needed vaccination programs to accelerate bTB control in high prevalence human and bovine TB settings where it is needed the most. Specifically, the inventors have identified polypeptide fragment combinations that serve as effective diagnostic reagents, while at the same time being straightforward to manufacture, store, regulate and operate.

According to a first aspect, the present invention provides a skin test diagnostic reagent comprising: at least one 40mer polypeptide consisting of any one of SEQ ID NOs: 1, 3 or 4 (each of which is a 40mer polypeptide fragment of ESAT-6); at least one 40mer fragment consisting of any one of SEQ ID NOs: 7 or 8 (each of which is a 40mer polypeptide fragment of CFP-10); and at least one 40mer polypeptide consisting of any one of SEQ ID NOs: 10, 11 or 12 (each of which is a 40mer polypeptide fragment of Rv3615c), characterised in that the reagent elicits a positive result when administered in a skin test to an animal infected with *Mycobacterium bovis* or *Mycobacterium tuberculosis*.

A skin test diagnostic reagent which comprises defined peptides or proteins having antigenic capability may be referred to as a defined antigen skin test (DST), when administered in a skin test to an animal. It will be appreciated that the term "DST reagent" is applicable to any skin test diagnostic reagent comprising defined peptides or proteins having antigen capability, when administered in a skin test to an animal.

Thus, the skin test diagnostic reagent of the present invention may be referred to as a DST reagent comprising at least one 40mer polypeptide consisting of any one of SEQ ID NOs: 1, 3 or 4 (each of which is a 40mer polypeptide fragment of ESAT-6); at least one 40mer fragment consisting of any one of SEQ ID NOs: 7 or 8 (each of which is a 40mer polypeptide fragment of CFP-10); and at least one 40mer polypeptide consisting of any one of SEQ ID NOs: 10, 11 or 12 (each of which is a 40mer polypeptide fragment of Rv3615c), characterised in that the reagent elicits a positive result when administered in a skin test to an animal infected with *Mycobacterium bovis* or *Mycobacterium tuberculosis.*

Reference to "40mer polypeptide" herein is reference to a 40mer polypeptide fragment of ESAT-7, CFP-10, or Rv3615c, as appropriate. Therefore, the term "40mer polypeptide" and "40mer polypeptide fragment" may be used interchangeably herein.

The inventors have found that the identified 40mer polypeptides, with at least one 40mer polypeptide from each of ESAT-6, CFP-10 and Rv3615c, provide for skin test diagnostic reagents with enhanced properties over previous tests. For example, the inventors have identified that skin test diagnostic reagents having these fragments show improved sensitivity over the SICCT test. In the experimentally infected animal population represented in FIG. 3, the SICCT test (B-A) identifies all animals as positive. A skin test diagnostic reagent of the invention (referred to as PCL, see Table 1 for components of PCL) provides at least the same sensitivity, as it also successfully identifies all animals as positive. In the animal population represented in FIG. 5A and FIG. 5B, the SICCT test identifies 12 of the 25 animals as positive, whereas PCL identifies 19 of the same 25 animals as positive. FIG. 6 shows this comparison in more detail, where of the 13 animals identified as negative in the SICCT test (solid squares and empty circles), 9 were identified as positive using PCL (solid squares). Likewise, another skin test diagnostic reagent of the invention (referred to as PC-1, see Table 1) identifies 17 of the 25 animals as positive, and FIG. 7 shows that of the 13 animals identified as negative in the SICCT test (empty circles) 8 were identified as positive using PC-1. It is important to remember that the SICCT test does not have DIVA potential, which is another benefit the reagents of the invention have over the SICCT test. In addition, the data also show that skin test diagnostic reagents of the invention (PCL and PC-1) have improved sensitivity with respect to previous polypeptide cocktails. For example, the sensitivity of the prior art cocktail of ESAT-6, CFP-10 and Rv3615c fragments shown in FIG. 1 gave a sensitivity of detecting 10/15 SICCT-test positive animals (i.e. 67%). The sensitivity provided by PCL and PC-1 (FIGS. 6 and 7) is 10/12 animals (83%) and 9/12 animals (75%) respectively.

The present invention obviates the need for full-length proteins, such as the ESAT-6, CFP-10 or Rv3615c proteins, and therefore also circumvents the challenges associated with production and purification of recombinant proteins, reproducible manufacture and preventing spoilage in storage. In a preferred embodiment, the skin test diagnostic reagents do not comprise any one or more of the full-length ESAT-6, CFP-10 or Rv3615c proteins.

The skin test diagnostic reagent allows for the user to distinguish animals infected with *Mycobacterium bovis* or *Mycobacterium tuberculosis* from animals that have not been infected with *Mycobacterium bovis* or *Mycobacterium tuberculosis* and, importantly, from animals that have been vaccinated against *Mycobacterium bovis* or *Mycobacterium tuberculosis.* The vaccinated animal can be, for example, an animal vaccinated with the live attenuated vaccine BCG. By "animal infected with", we are referring to animals that have been infected with or exposed to *Mycobacterium bovis* or *Mycobacterium tuberculosis* such that antibodies have been raised against these bacteria. The infection can be a previous infection, including an infection that has been treated, cured, or naturally overcome or suppressed by the host animal. The animal may be a mammal, such as a cow, a badger or a human.

In one embodiment, the skin test diagnostic reagent comprises at least four, five, six or seven different polypeptides, each selected from a 40mer polypeptide consisting of SEQ ID NOs: 1, 3, 4, 7, 8, 10, 11 and 12, or a functional variant thereof. In a preferred embodiment, the skin test diagnostic reagent comprises each of the 40mer polypeptides consisting of SEQ ID NOs: 1, 3, 4, 7, 8, 10, 11 and 12, or a functional variant thereof. In a particularly preferred embodiment, the skin test diagnostic reagent comprises each of the 40mer polypeptides consisting of SEQ ID NOs: 1, 3, 4, 7, 8, 10, 11 and 12. By "different" polypeptides or polypeptide fragments, we are referring to polypeptides that are different in sequence from others in the reagent.

The present invention also encompasses skin test diagnostic reagents comprising functional variants of the identified polypeptides and methods utilising these variant polypeptide fragments. That is, where provided for, the polypeptide can be selected from the base amino acid sequence given in each SEQ ID NO, or can be a functional variant of the base sequence. By "functional", we mean that the variant still elicits a positive result when administered in a skin test to an animal infected with *Mycobacterium bovis* or *Mycobacterium tuberculosis.* In a particularly preferred embodiment, the fragments having the base sequence are used.

The skin test diagnostic reagent can comprise at least one, preferably two, more preferably three or, yet more preferably, four further different polypeptides, each selected from: a 40mer polypeptide consisting of SEQ ID NOs: 2, 5, 6 and 9, or a functional variant thereof; and a 20mer polypeptide consisting of SEQ ID NO: 38, or a functional variant thereof. In a preferred embodiment, the skin test diagnostic reagent comprises each of the 40mer polypeptides consisting of SEQ ID NOs: 1, 2, 3, 4, 5, 6, 7, 8, 9, 10, 11 and 12, or a functional variant thereof, and the 20mer polypeptide consisting of SEQ ID NO: 38, or a functional variant thereof.

In a particularly preferred embodiment, the skin test diagnostic reagent comprises each of the 40mer polypeptides consisting of SEQ ID NOs: 1, 2, 3, 4, 5, 6, 7, 8, 9, 10, 11 and 12 and the 20mer polypeptide consisting of SEQ ID NO: 38. In particular, the peptidic (including proteinaceous) components of the skin test diagnostic reagent consists of, or consists essentially of, each of the 40mer polypeptides consisting of SEQ ID NOs: 1, 2, 3, 4, 5, 6, 7, 8, 9, 10, 11 and 12 and the 20mer polypeptide consisting of SEQ ID NO: 38.

The skin test diagnostic reagent can further comprise at least one, preferably two or, more preferably, three further different polypeptides, each selected from: a 20mer polypeptide consisting of SEQ ID NOs: 17, 25, 36 and 39, or a functional variant thereof. In a preferred embodiment, the skin test diagnostic reagent comprises each of the 40mer polypeptides having SEQ ID NOs: 1, 3, 4, 7, 8, 10, 11 and 12, or a functional variant thereof, and each of the 20mer polypeptides having SEQ ID NOs: 17, 25, 36 and 39, or a functional variant thereof.

In a particularly preferred embodiment, the skin test diagnostic reagent comprises each of the 40mer polypeptides having SEQ ID NOs: 1, 3, 4, 7, 8, 10, 11 and 12, and each of the 20mer polypeptides having SEQ ID NOs: 17, 25, 36 and 39. In particular, the peptidic (including proteinaceous) components of the skin test diagnostic reagent consists of, or consists essentially of, each of the 40mer polypeptides having SEQ ID NOs: 1, 3, 4, 7, 8, 10, 11 and 12, and each of the 20mer polypeptides having SEQ ID NOs: 17, 25, 36 and 39

In a particularly preferred embodiment, the skin test diagnostic reagent comprises each of the 40mer polypeptides consisting of SEQ ID NOs: 1, 2, 3, 4, 5, 6, 7, 8, 9, 10, 11 and 12 and the 20mer polypeptide consisting of SEQ ID NO: 38; or each of the 40mer polypeptides having SEQ ID NOs: 1, 3, 4, 7, 8, 10, 11 and 12, and the 20mer polypeptides having SEQ ID NOs: 17, 25, 36 and 39.

In an embodiment, the skin test diagnostic reagent comprises no more than 15, no more than 14, no more than 13, no more than 12, no more than 11 or no more than 10 different polypeptides. Each different polypeptide may be selected from each of SEQ ID NOs: 1, 2, 3, 4, 5, 6, 7, 8, 9, 10, 11, 12, 17, 25, 36, 38 and 39, or a functional variant thereof.

In a particularly preferred embodiment, the peptidic (including proteinaceous) components of the skin test diagnostic reagents consist essentially of amino acid chains having less than 80 sequential amino acids, for example less than 70, 60, 55, 50 or 46 sequential amino acids. Typically, the amino acid chains will have greater than 10 sequential amino acids, for example greater than 12, 13, 14, 15, 16, 17 or 18 consecutive amino acids.

The skin test diagnostic reagent may comprise one or more adjuvants and/or excipients. However, in one embodiment, the skin test diagnostic reagent does not comprise an adjuvant, i.e., a reagent that assists in propagating an immune response to enhance the effect of the diagnostic reagent, but which does not itself induce an immune response. An example is a bacterial lipopeptide and the skilled person is readily able to determine the identity of a suitable adjuvant in a given context. It is preferable to avoid the use of adjuvants in a skin test reagent, since repeat skin test injections (as is required to monitor the health of, for example, a herd of dairy cattle) may lead to the sensitisation of non-*tuberculosis* infected animals, so that the skin test would cease to be useful to differentiate between infected animals and uninfected but vaccinated animals.

The skin test referred to herein may be any of a CFT, SIT or SICCT test, as described in the Office International des Epizooties (OIE) Manual of Diagnostic Tests and Vaccines for Terrestrial Animals (available at www.oie.int/standard-setting/terrestrial-manual/access-online/, accessed 15 Mar. 2019). The manual provides information, definitions and guidelines on positive test criteria. Therefore, when the diagnostic reagent according to the invention elicits a positive result when administered in a skin test such as one of those mentioned above, this is determined, for example, by detection of an increased thickness and/or induration of skin at the site at which the diagnostic reagent has been injected, using calipers, for example. The skin thickness may ideally be determined, for example, prior to injection (to provide a starting thickness for comparison after injection) and at one or more of, for example, about 24, 36, 48, 72, 96 or about 120 hours after injection of the diagnostic reagent. Determining skin thickness at about 72 hours after injection is typical. Thickness may be determined at any time period after injection, provided that, when results from different tests are compared, they are compared after substantially the same time period after injection (e.g., between 1 and 10 hours before or after one of the time points mentioned above such as the 72 hour time point, for example, between 3 and 7 hours before or after or about 5 hours before or after).

The diagnostic reagent may be in the form of a sterile injectable preparation which may be an aqueous or an oleaginous suspension, or a suspension in a non-toxic parenterally-acceptable diluent or solvent. The aqueous suspension may be prepared in, for example, mannitol, water, Ringer's solution or isotonic sodium chloride solution. Alternatively, it may be prepared in phosphate buffered saline solution. The oleaginous suspension may be prepared in a synthetic monoglyceride, a synthetic diglyceride, a fatty acid or a natural pharmaceutically-acceptable oil. The fatty acid may be an oleic acid or an oleic acid glyceride derivative. The natural pharmaceutically-acceptable oil may be an olive oil, a castor oil, or a polyoxyethylated olive oil or castor oil. The oleaginous suspension may contain a long-chain alcohol diluent or dispersant, for example, Ph. Helv.

According to a second aspect, the invention provides a skin test diagnostic reagent according to the first aspect of the invention, for use in a method of detecting Myobacterium *bovis* or *Mycobacterium tuberculosis* infection in an animal.

According to a third aspect, the invention provides a method of detecting *Mycobacterium bovis* or *Mycobacterium tuberculosis* infection in an animal comprising conducting a skin test on the animal using at least one skin test diagnostic reagent according to the first aspect of the invention. The animal can be a mammal, for example a cow, a badger or a human. The method may further comprise a step of correlating a positive skin test result with infection of an animal with Myobacterium *bovis* or *Mycobacterium tuberculosis* and a step of diagnosing said animal as being infected by Myobacterium *bovis* or *Mycobacterium tuberculosis*.

"Using" and "use" of polypeptides and diagnostic reagents in the skin test included in method according to this aspect of the invention typically involves intradermal injection of the diagnostic reagent into the animal. A skin test for use in the invention may be conducted as described in OIE Manual of Diagnostic Tests and Vaccines for Terrestrial Animals, as mentioned above.

According to a fourth aspect, the invention provides a skin test diagnostic reagent according to the first aspect of the invention for use in a method of diagnosing infection of an animal by *Mycobacterium bovis* or *Mycobacterium tuberculosis*, the method comprising the steps of conducting a method according to the third aspect of the invention on the animal and correlating a positive skin test result with infection of the animal by *Mycobacterium bovis* or *Mycobacterium tuberculosis*.

According to a fifth aspect, the invention provides a diagnostic kit comprising a skin test diagnostic reagent according to the first, second or fourth aspects of the invention. The diagnostic kit can be for use in a method according to the third aspect of the invention. Preferably, the diagnostic kit comprises a diagnostic reagent wherein the diagnostic reagent is able to detect a *Mycobacterium bovis* or *Mycobacterium tuberculosis* infection in a mammal. Preferably, the diagnostic reagent is able to differentiate between a *Mycobacterium bovis* or *Mycobacterium tuberculosis* infected mammal and a mammal vaccinated against *Mycobacterium bovis* or *Mycobacterium tuberculosis* infection.

The diagnostic reagent of the kit can be in liquid form and included in at least one aliquot of 0.05-0.15 ml containing 1-20 µg of each polypeptide contained in the skin test diagnostic reagent. For example, the kit may comprise aliquots of about 0.05 ml, about 0.06 ml, about 0.07 ml, about 0.08 ml, about 0.09 ml, about 0.1 ml, about 0.11 ml, about 0.12 ml, about 0.13 ml, about 0.14 ml or about 0.15 ml, containing 1-20 µg, for example, 3-18 µg or 5-15 µg of each epitope polypeptide, for example, about 5 µg, about 6 µg, about 7 µg, about 8 µg, about 9 µg, about 10 µg, about 11 µg, about 12 µg, about 13 µg, about 14 µg or about 15 µg of each epitope polypeptide. Each aliquot may be contained in a disposable injection device. The kit may further comprise at least one sample of PPD. The diagnostic reagent may be able to detect a *M. bovis* or *M. tuberculosis* infection in a mammal and may be able to differentiate between an *M. bovis-* or *M. tuberculosis*-infected mammal and a mammal vaccinated against infection by *M. bovis* or *M. tuberculosis*.

The present invention also encompasses skin test diagnostic reagents comprising functional variants of the identified polypeptides and methods utilising these variant polypeptides. For example, the skin test diagnostic reagents according to the aspects of the invention may further comprise one or more functional variants of the identified polypeptides. The variant is still functionally active in that it still elicits a positive result when administered in a skin test to an animal infected with *Mycobacterium bovis* or *Mycobacterium tuberculosis*.

As used herein, a "variant" means a polypeptide in which the amino acid sequence differs from the base sequence from which it is derived in that one or more amino acids within the sequence are substituted for other amino acids. The variant is a functional variant, in that the functional characteristics of the polypeptide from which the variant is derived are maintained. For example, a similar immune response is elicited by exposure of an animal, or a sample from an animal, to the variant polypeptide as to the non-variant. Specifically, the functional variant still elicits a positive result when administered in a skin test to an animal infected with *Mycobacterium bovis* or *Mycobacterium tuberculosis*. In particular, any amino acid substitutions, additions or deletions must not alter or significantly alter any tertiary structure of one or more epitopes contained within the polypeptide from which the variant is derived. The skilled person is readily able to determine appropriate functional variants and to determine the tertiary structure of an epitope and any alterations thereof, without the application of inventive skill.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

As mentioned above, non-conservative substitutions are possible provided that these do not disrupt the tertiary structure of an epitope within the polypeptide, for example, which do not interrupt the immunogenicity (for example, the antigenicity) of the polypeptide.

Broadly speaking, fewer non-conservative substitutions will be possible without altering the biological activity of the polypeptide. Suitably, variants may be at least 50% identical, 60% identical, for example at least 75%, 80%, 85%, 86%, 87%, 88%, 89%, 90%, 91%, 92%, 93%, 94%, 95%, 96%, 97%, 97.5%, 98% or at least 99% identical to the base sequence.

Sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. The percentage sequence identity may be determined using the BLASTP software, publicly available at blast.ncbi.nlm.nih.gov/ Blast.cgi (accessible on 18 Apr. 2011), using default parameter settings. The amino acid sequence identity may be determined at a global level (otherwise known as "global sequence identity"), between a first and a second sequence.

Determination of sequence identity at a global level may be carried out using, for example, the Needleman-Wunsch Global Sequence Alignment Tool also available via the NCBI Blast® internet site (blast.ncbi.nlm.nih.gov/ Blast.cgi). This tool allows a user to compare two sequences across their entire span.

Where the base sequence is a 40mer polypeptide, we are referring to a polypeptide fragment that consists of 40 amino acids. Where the polypeptide fragment is a variant, the polypeptide can have 40 amino acids or can have a number of amino acids higher or lower than 40 by up to 5 amino acids. For example, amino acids may be added to or removed from the N- and/or C-terminus of the polypeptide described herein. For example, the variant polypeptide fragment may consist of between 35 and 45 amino acids, between 37 and 43 amino acids or between 39 and 41 amino acids, such as consisting of 35, 36, 37, 38, 39, 40, 41, 42, 43, 44 or 45 amino acids. This length of polypeptide can be selected individually for each variant in the diagnostic reagent. In a preferred embodiment, the variant polypeptide consists of 40 amino acids. The variant polypeptide may comprise an amino acid substitution, such as a conservative amino acid substitution as outlined above, at 1, 2, 3, 4, 5, 6, 7, 8, 9 or 10 positions within a polypeptide sequence provided herein as SEQ ID NOs: 1-44. That is, the variant sequence is identical to the sequence specified herein, with the exception of the one or more substitutions, or comprises such a variant sequence and an additional up to 5 amino acids at the N- or C-terminus of the sequence.

Throughout the description and claims of this specification, the words "comprise" and "contain" and variations of the words, for example "comprising" and "comprises", mean "including but not limited to", and do not exclude other components, integers or steps. Moreover the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

The invention will now be described, by way of example only, with reference to the accompanying drawings, in which.

DETAILED DESCRIPTION

Materials and Methods

Figure 1:
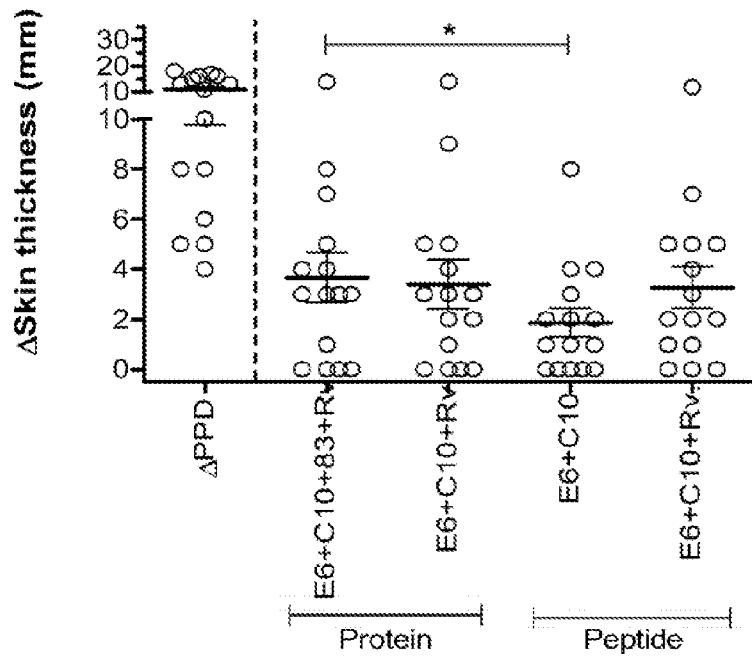
FIG. 1 (Prior Art) was originally published in WO 2011/135369 as FIG. 8 and shows the skin-test performance of a series of reagents tested in SICCT-test positive (reactor) cattle (n=15). The PPD column shows the results of the SICCT test. The next two columns show the results of using cocktails of full-length proteins: an ESAT6/CFP10/MPB83/Rv3615c protein cocktail and an ESAT6/CFP10/Rv3615c protein cocktail. The final two columns show the results of using cocktails of peptides: an ESAT6/CFP10 peptide cocktail and an ESAT6/CFP10/Rv3615c peptide cocktail.

Antigens and peptides. Commercial preparations of bovine tuberculin (PPD-B) and avian tuberculin (PPD-A, Thermo Fisher) were used to stimulate PBMCs at a final concentration of 300 and 250 IU/ml, respectively, as per kit instructions. Two sets of peptides (PCL, 40-mer length with a 20-residue overlap; or PCS, 16 to 20-mers with an 8-12 residue overlap) were chemically synthesized to a minimal purity of 98 and 85%, respectively. The identity was confirmed by mass spectrometry (see Table. S1 for amino acid sequences).

Animals. For the in vitro experiments conducted at Animal and Plant Health Agency (APHA), archived PBMC from the following groups of cattle (*Bos taurus taurus*) were used. (i) Naturally *M. bovis*-infected cattle originating from UK herds known to have bTB (natural infection was confirmed by post mortem and/or culture analysis). (ii) Non-infected control cattle originating from UK herds in the Low Risk Area that were Officially TB Free for over 5 years. (iii) BCG vaccinates consisting of control cattle as described in (ii) that were subsequently vaccinated with BCG Danish SSI (equivalent to 5 human doses). PBMC from 8 weeks post vaccination were used. For in vivo testing of the peptide cocktails, the following groups of cattle were used. (i) Experimentally *M. bovis* infected cattle consisting of male calves experimentally infected with approx. 10,000 CFU of a field strain of *M. bovis* (AF2122/97) via the endobronchial route. Skin tests were performed 5 or 6 weeks post infection, and infection was confirmed by post mortem and/or culture analysis. (ii) Non-infected control cattle as described above.

To determine performance characteristics of the skin test diagnostic reagent (also referred to as the defined skin test, or DST) in endemic country settings, in vivo sensitivity of the peptide cocktails was also assessed in twenty-five adult crossbred (Holstein Friesian×Zebu) cattle in Ethiopia. These cattle were initially recruited from the Holeta National Dairy Research Centre of the Ethiopian Institute of Agricultural Research as they were positive for bTB, and gave strong positive responses to both SICCT and IGRA. All cattle experiments conducted at this Centre were performed in accordance with animal ethics and biosafety protocols approved by the Aklilu Lemma Institute of Pathobiology Review Board (Ref. No. ALIPB IBR/007/2011/2018).

In order to assess the skin test performance of the skin test diagnostic reagent in vaccinated animals, 3-6-month old crossbred calves (*Bos taurus* ssp. *taurus*×*Bos taurus* ssp. *indicus*) were recruited from bTB-free farms near Chennai, India. Following recruitment, calves were housed in facilities at the Tamil Nadu Veterinary and Animal Sciences University (TANUVAS) and screened for helminths and dewormed during the acclimatization period. During the trial period, calves were fed with milk initially and then with concentrate, green fodder and water ad libitum. Freeze-dried preparations of BCG Danish strain were obtained from Green Signal Bio Pharma Pvt. Ltd., India. These were reconstituted as per manufacturer instructions and colony counts were performed. Calves were randomly assigned to two groups of 15 each using the double lottery principle. The vaccinates were administered a single dose equivalent of 5 human doses ($1\text{-}4\times10^6$ CFU of BCG Danish) subcutaneously at approximately 3 to 6 months of age. All cattle experiments in India were approved by the Institutional Animal Ethics Committee (IAEC) at TANUVAS and Committee for the Purpose of Control and Supervision of Experimental Animals (CPCSEA; F. No. 25/31/2017-CPCSEA).

Animal procedures for studies conducted at APHA were approved by the APHA Animal Welfare and Ethical Review Body and in Ethiopia by the AAU Ethics review committee.

Skin test procedures. PPD-A and PPD-B were administered in a 0.1-ml volume as per manufacturer's recommendations while peptides were administered as a cocktail containing 10 µg of each peptide (0.1-ml final volume). Skin thicknesses were measured by the same operator before and after 72 hours after administration, and the difference in skin thickness (mm) between the pre- and post-skin test readings was recorded as per OIE prescribed guidelines (21).

In vitro stimulation of PBMC. The PBMC preparation was performed following the "Overlay" method using tubes without frit and cryo-preserved. Thawing of cryo-preserved cells was performed as quickly as possible in a water bath at 37° C. Upon thawing, appropriate volume of complete media (RPMI 1640 containing 2 mM GlutaMax, 25 mM HEPES, 0.1 mM NEAA, $5\times10^{-5}$ M β-mercaptoethanol, 100 U/ml penicillin, 100 µg/ml streptomycin (Gibco Life Technologies, UK) and 10% fetal calf serum (Sigma-Aldrich, UK)) was added in a drop-by-drop manner and centrifuged at 350 g for 10 minutes at room temperature. The supernatant was carefully discarded, and the cell pellet was gently loosened, following which it was resuspended in an appropriate volume of fresh complete media depending on the required concentration for the assay. Cells were counted using a hemocytometer and incubated with the antigens for in vitro stimulation. For ELISPOT/FluoroSpot, following an incubation period of ~20 hours, the spots were developed as described below. For BOVIGAM, the incubation period was 3-5 days, after which the plates were centrifuged at 350 g for 10 minutes at room temperature and the supernatant was carefully harvested.

IFN-γ ELISA. IFN-γ concentrations in PBMC culture supernatants were determined using the commercially available BOVIGAM enzyme-linked immunosorbent assay (ELISA)-based kits (Thermo Fisher Scientific, USA). Results were initially expressed as the optical density at 450 nm ($OD_{450}$) for cultures stimulated with antigen minus the $OD_{450}$ for cultures without antigen (i.e. $\Delta OD_{450}$). The results from antigen dose titration curves allowed Area Under the Curve (AUC) values to be calculated using Prism 7 (Graphpad Software, La Jolla, CA) software.

IFN-γ ELISpot/FluoroSpot assay. Stimulation of PBMC for these assays was performed as previously described (40). The production of IFN-γ by PBMCs was detected using either: (i) a secondary biotinylated antibody followed by incubation with streptavidin-linked horseradish peroxidase (bovine IFN-γ ELISpot kit: Mabtech, Stockholm, Sweden), with visualization using an AEC chromogen kit (Sigma, St. Louis, MO) and spot forming units counted using an AID ELISPOT reader and ELISpot 4.0 software (Autoimmun Diagnostika, Germany); or (ii) a secondary BAM-conjugated anti-bovine IFN-γ antibody (clone MT307, Mabtech) followed by incubation with a fluorophore-labelled anti-BAM-490 (Mabtech) antibody, with visualization using a fluorescence enhancer (Mabtech. Spot forming units were counted using an ELISpot/FluoroSpot reader system (iSpot Spectrum, AID, Germany) with software version 7.0.

Statistical Analysis. All statistical analyses were performed using Prism 7 (Graphpad Software, La Jolla, CA).

TABLE 1

| SEQ ID NO | Nomenclature | Polypeptide sequence |
|---|---|---|
| 1 | EL1 | MTEQQWNFAGIEAAASAIQGNVTSIHSLLDEGKQSLTKLA |
| 2 | EL2 | NVTSIHSLLDEGKQSLTKLAAAWGGSGSEAYQGVQQKWDA |
| 3 | EL3 | AAWGGSGSEAYQGVQQKWDATATELNNALQNLARTISEAG |
| 4 | EL4 | TATELNNALQNLARTISEAGQAMASTEGNVTGMFA |
| 5 | CL1 | MAEMKTDAATLAQEAGNFERISGDLKTQIDQVESTAGSLQ |
| 6 | CL2 | ISGDLKTQIDQVESTAGSLQGQWRGAAGTAAQAAVVRFQE |
| 7 | CL3 | GQWRGAAGTAAQAAVVRFQEAANKQKQELDEISTNIRQAG |
| 8 | CL4 | AANKQKQELDEISTNIRQAGVQYSRADEEQQQALSSQMGF |
| 9 | RL1 | MTENLTVQPERLGVLASHHDNAAVDASSGVEAAAGLGESV |
| 10 | RL3 | AITHGPYCSQFNDTLNVYLTAHNALGSSLHTAGVDLAKSL |

TABLE 1-continued

| SEQ ID NO | Nomen-clature | Polypeptide sequence |
|---|---|---|
| 11 | RL4 | AHNALGSSLHTAGVDLAKSLRIAAKIYSEADEAWRKAIDG |
| 12 | RL5 | RIAAKIYSEADEAWRKAIDGLFT |
| 13 | ES1 | MTEQQWNFAGIEAAAS |
| 14 | ES2 | AGIEAAASAIQGNVTS |
| 15 | ES3 | AIQGNVTSIHSLLDEG |
| 16 | ES4 | IHSLLDEGKQSLTKLA |
| 17 | ES5 | KQSLTKLAAAWGGSGS |
| 18 | ES6 | AAWGGSGSEAYQGVQQ |
| 19 | ES7 | EAYQGVQQKWDATATE |
| 20 | ES8 | KWDATATELNNALQNL |
| 21 | ES9 | LNNALQNLARTISEAG |
| 22 | ES10 | ARTISEAGQAMASTEG |
| 23 | ES11 | QAMASTEGNVTGMFA |
| 24 | CS1 | MAEMKTDAATLAQEAGNF |
| 25 | CS2 | QEAGNFERISGDLKTQ |
| 26 | CS3 | ERISGDLKTQIDQVESTA |
| 27 | CS4 | IDQVESTAGSLQGQWRG |
| 28 | CS5 | GSLQGQWRGAAGTAAQAA |
| 29 | CS6 | AGTAAQAAVVRFQEAANK |
| 30 | CS7 | VVRFQEAANKQKQELDEI |
| 31 | CS8 | QKQELDEISTNIRQAGVQYS |
| 32 | CS9 | NIRQAGVQYSRADEEQQQ |
| 33 | CS10 | RADEEQQQALSSQMGF |
| 34 | RS1 | MTENLTVQPERLGVLASHHD |
| 35 | RS2 | PERLGVLASHHDNAAVDASS |
| 36 | RS3 | SHHDNAAVDASSGVEAAAGL |
| 37 | RS4 | DASSGVEAAAGLGESVAITH |
| 38 | RS5 | AAGLGESVAITHGPYCSQFN |
| 39 | RS6 | AITHGPYCSQFNDTLNVYLT |
| 40 | RS7 | SQFNDTLNVYLTAHNALGSS |
| 41 | RS8 | VYLTAHNALGSSLHTAGVDL |
| 42 | RS9 | LGSSLHTAGVDLAKSLRIAA |
| 43 | RS10 | GVDLAKSLRIAAKIYSEADE |
| 44 | RS11 | RIAAKIYSEADEAWRKAIDG |

Table 1. Polypeptide fragments. All short and long peptides used in the study are listed and sequences are provided.
PCL constitutes: EL1 to EL4, CL1 to CL4, RL1, RL3 to RLS and RS5.
Note:
RL2 could not be synthesized due to technical difficulties and RS5 was included as part of PCL to cover the gap in the overlap left by the absence of RL2.
PC-1 constitutes: EL1 EL3, EL4, CL3, CL4, RL3, RL4, RL5, ES5, CS2, RS3 and RS6.

Results

Figure 2:
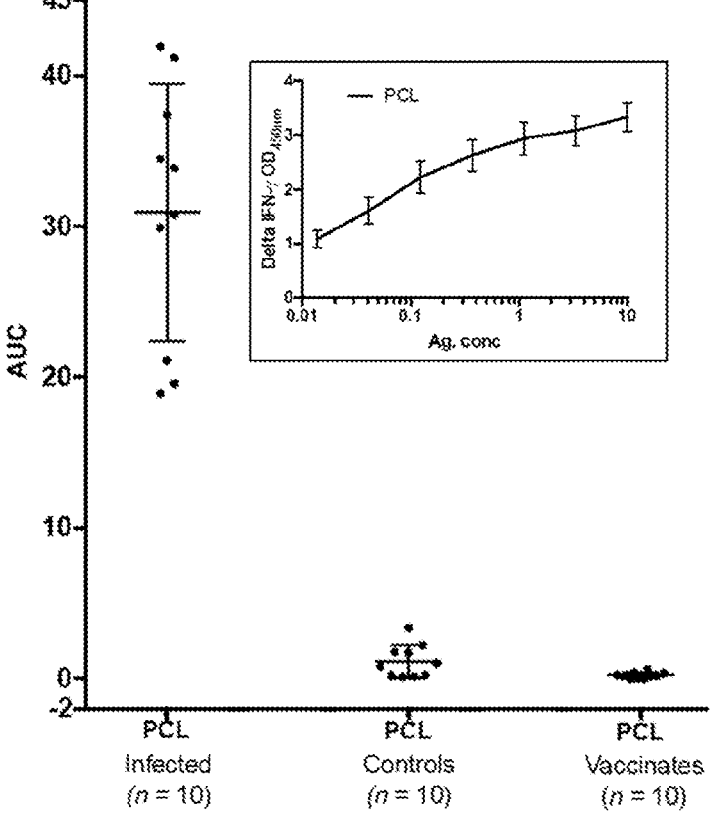
FIG. 2 shows the capacity of the PCL antigen to induce in vitro IFN-γ response in peripheral blood mononuclear cells (PMBCs) collected from naturally *M. bovis* infected cattle (n=10), naïve cattle (n=10) and BCG vaccinates (n=10). The antigens were used at titrated dose concentrations and area under the curve (AUC) is plotted. The horizontal line provides the mean (±standard deviation). The background-corrected OD values of the PCL antigen at each titrated concentration tested are shown in the inset.

Defined antigens elicit a sensitive and specific in vitro IFN-γ and skin test response in bTB infected cattle. A comparison of the performance of a peptide cocktail composed primarily of 40mer peptides covering the sequences of ESAT-6, CFP-10 and Rv3615c with 20 residues overlap (referred to as PCL) was undertaken using IGRAs with PBMCs isolated from naturally M. bovis infected cattle, naïve controls and BCG vaccinates. The IGRAs were preformed to establish a dose response relationship and the results were expressed as Area Under the Curves (AUC, FIG. 2). The data demonstrated that PCL induced strong in vitro interferon-γ (IFN-γ) responses in infected cattle, in contrast to inducing minimal, if any, IFN-γ responses in PBMCs from control or vaccinated animals, suggesting potential utility of defined antigens in in vitro IFN-γ assays to specifically identify M. bovis infected cattle.

Figure 3:
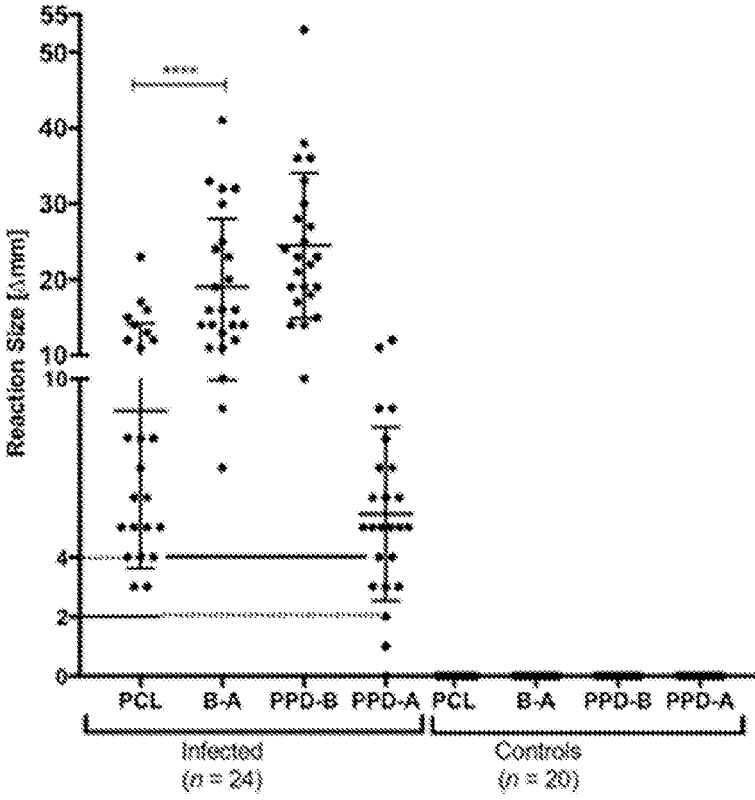
FIG. 3 shows skin-test performance of a series of reagents measured at 72 hours post-injection in cattle experimentally infected with *M. bovis* (n=24) and naïve controls (n=20). The reagents tested include the peptide cocktail PCL (of ESAT6/CFP10/Rv3615c peptide fragments), the SICCT test result (B-A) and the raw data for the SICCT test is given in the PPD-B and PPD-A columns. The horizontal line provides the median (±95% CI). The statistical difference between the responses was determined using ANOVA (****, P<0.0001). The solid horizontal line at 4 mm is the cut-off used for B-A and PPD-B. The solid horizontal line at 2 mm is the cut-off used for PCL.

The performance of PCL as a defined skin test antigen (i.e. a DST antigen) was next assessed in animals experimentally infected with M. bovis (n=24). The results showed that when applying the established strict interpretation criteria for positivity of 2 mm or more increase in skin induration reaction, PCL was able to correctly classify all of the infected animals as positive (FIG. 3). In contrast, PCL did not induce measurable skin induration responses in a control group of naïve animals (n=20). Together, these results suggest that PCL is able to accurately classify infected from uninfected animals with high apparent sensitivity and specificity.

Figure 8:
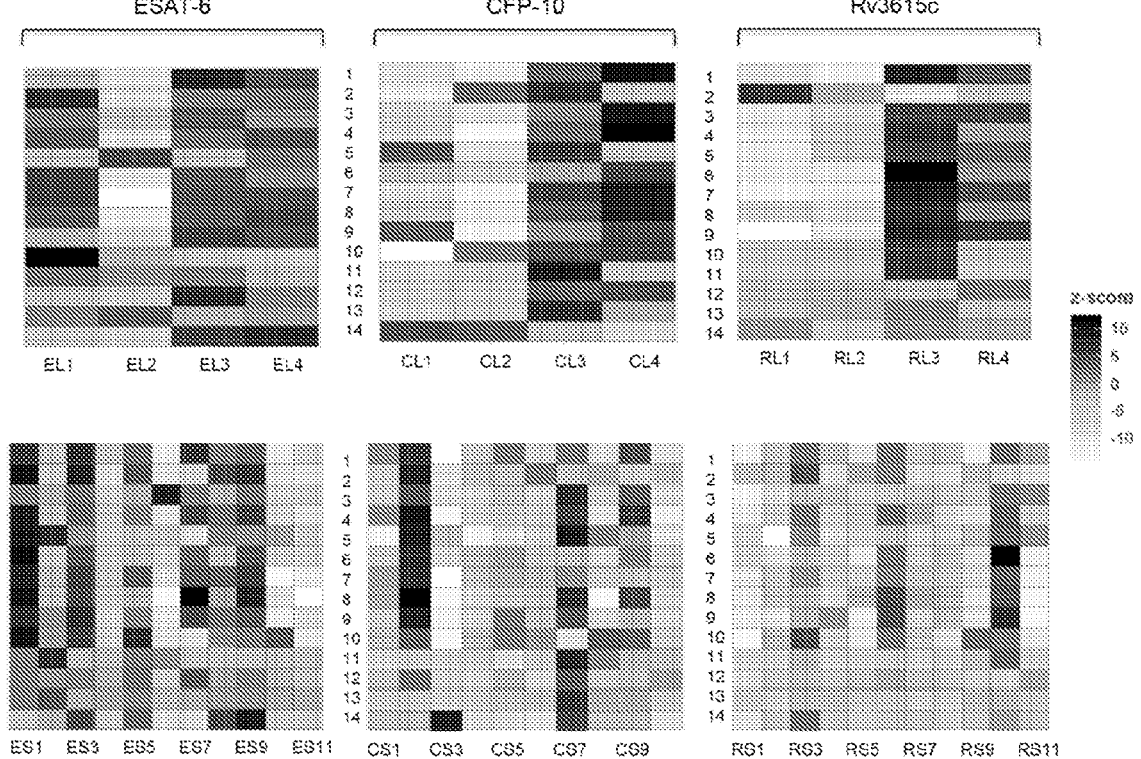
FIG. 8 is a heat map representing the IFN-γ response elicited by the individual long (top) and short (bottom) peptides of ESAT-6, CFP-10 and Rv3615c, using PBMCs isolated from naturally *M. bovis* infected cattle (n=14). The Z-scores of individual peptide responses in individual cattle are mapped. The peptides constituting PC-1 are marked with closed circles. RL2 could not be synthesised due to technical difficulties.

A subset of peptides drives a majority of the observed immune responsiveness in infected cattle. Next, we performed extensive experiments to identify immuno-dominant peptides within PCL in an attempt to develop a reduced complexity peptide cocktail consisting of the most dominant and promiscuously recognized peptides, as well as to identify likely epitopes by comparing with previous studies sets of smaller overlapping peptides (30). This also provided an opportunity to identify specific epitopic regions on the longer peptides that might be susceptible to inappropriate processing and to identify alternative peptides to mitigate this loss of immune recognition. Individual peptides from PCL and of a corresponding set of overlapping short, 16-20 amino acids long peptides were synthesized and screened for their individual ability to elicit IFN-γ responses in ELISPOT assays using PBMCs isolated from naturally M. bovis-infected cattle (n=14). Briefly, the numbers of cytokine-secreting cells elicited by stimulation with each peptide were determined. The statistical difference between the average response elicited in an individual animal for each protein and the response to individual peptides representing that particular protein was determined using z-scores and the results are mapped as shown in FIG. 8. The results show that a majority of the observed immune responsiveness within PCL and the shorter peptides are driven by only subset of peptides recognized promiscuously by almost every animal tested (FIG. 8). This result suggested that further refinement of the compositional complexity of PCL was possible. The data also suggest that some epitopes contained within the long peptides were not as well recognized as when they were represented on the shorter peptides (FIG. 8). For example, a strong epitope within ESAT-6 is localized within the short peptide 17. Consequently, the expectation was that 2 would be strong and promiscuously recognized as well. However, as FIG. 8 shows, peptide 2 was poorly and infrequently recognized. Other similar examples also occurred with peptides 5, which is poorly recognized, whilst the short peptide 25, whose sequence is contained in 5, is strongly recognized.

Similarly, 9 and 10, were poorly recognized but their poor recognition could be compensated by the short peptides 36 and 39 (FIG. 8).

Figure 4:
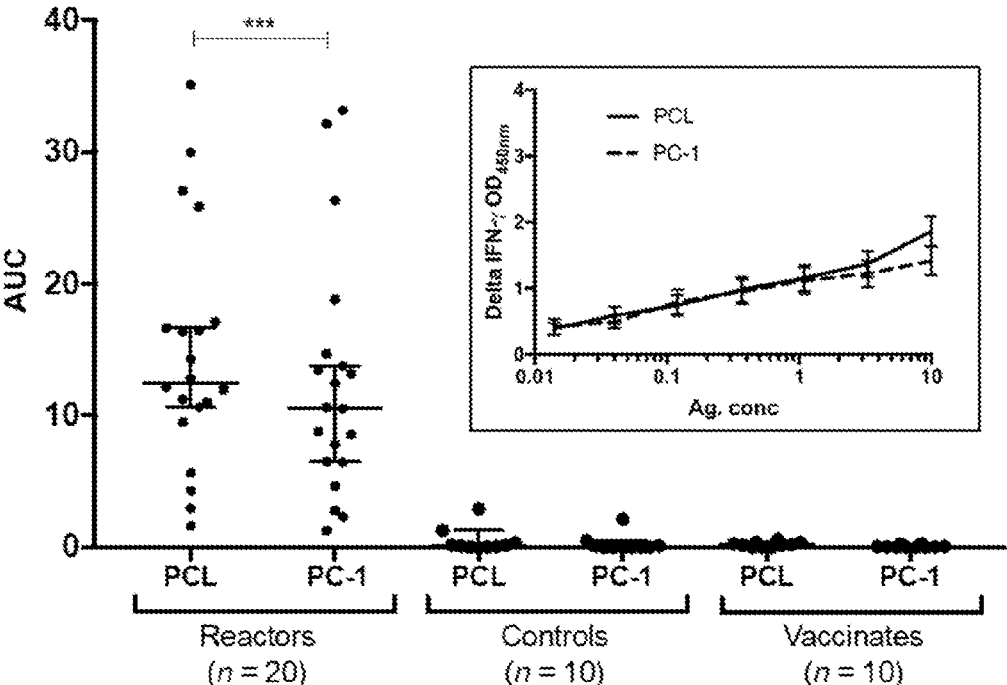
FIG. 4 shows the capacity of PCL and PC-1 to induce in vitro IFN-γ responses in PBMCs collected from naturally *M. bovis* infected cattle (n=20), BCG vaccinates (n=10) and controls (n=10). The antigens were used at titrated dose concentrations and the area under the curve (AUC) is plotted disregarding the highest concentration (10 μg/ml). The horizontal line provides the median (±95% CI), and the statistical difference between the responses for PCL and PC-1 in infected and controls was determined using the Wilcoxon matched-pairs signed rank test (*, P<0.05), while two-tailed t test was used for vaccinates (*, P<0.05). There is no significant difference between the responses induced by PCL and PC-1 in infected animals. The background-corrected OD values of PCL and PC-1 at each titrated concentration tested in infected animals are shown in the inset.

Optimized peptide cocktail PC1 displays comparative sensitivity and specificity as PCL. Based on the strength of immune response induced by individual peptides antigens and the sequence overlaps between PCL and shorter peptides, we assembled a cocktail (PC-1) representing a combination of promiscuously recognized long and short peptides (Table 1). The capability of PC-1 to induce an IFN-γ response was assessed with IGRAs performed on cryopreserved PBMCs isolated from known naturally infected cattle (n=20), naïve controls (n=10) and BCG vaccinates (n=10). The results showed that PCL induced a significantly stronger response in infected animals compared to PC-1 (P<0.001), though this was driven by a stronger response elicited by PCL at only the highest titrated dose concentration (10 μg/ml), but not others (FIG. 4 insert). This high concentration also induced non-specific IGRA responses in some of the naïve animals and is therefore not a peptide concentration that is diagnostically relevant due to its relative lack of specificity (data not shown). If this concentration was disregarded in calculating the areas under the curves, PCL and PC1 performed identically. Only limited, if any, IGRA responses based on evaluation of AUC values were induced by either cocktail when they were tested with PBMCs from naïve or BCG vaccinated animals (FIG. 4).

Figure 6:
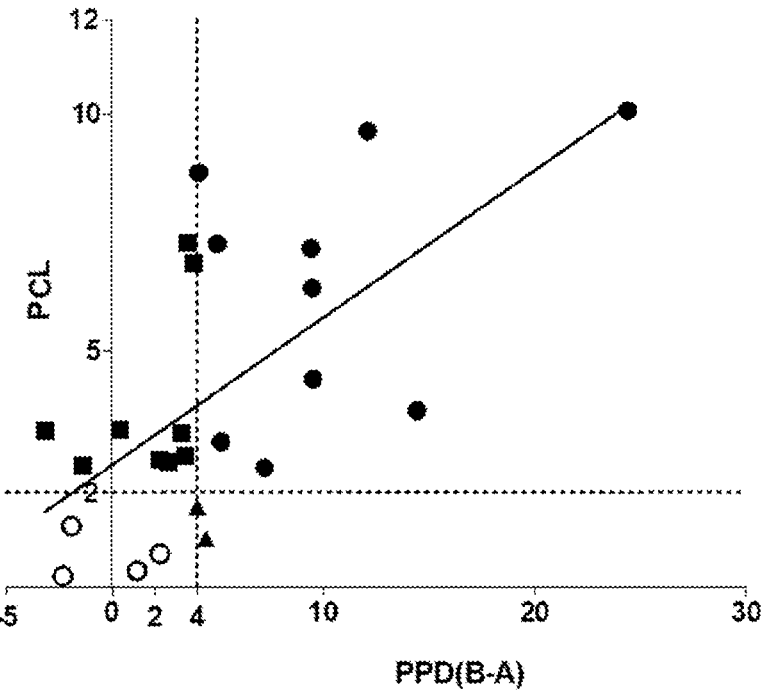
FIG. 6 shows how each of the animals represented in FIG. 5 responded to the SICCT test (PPD(B-A)) and to PCL. The open circles show SICCT-negative animals, and the closed circles show SICCT-positive animals.
Figure 7:
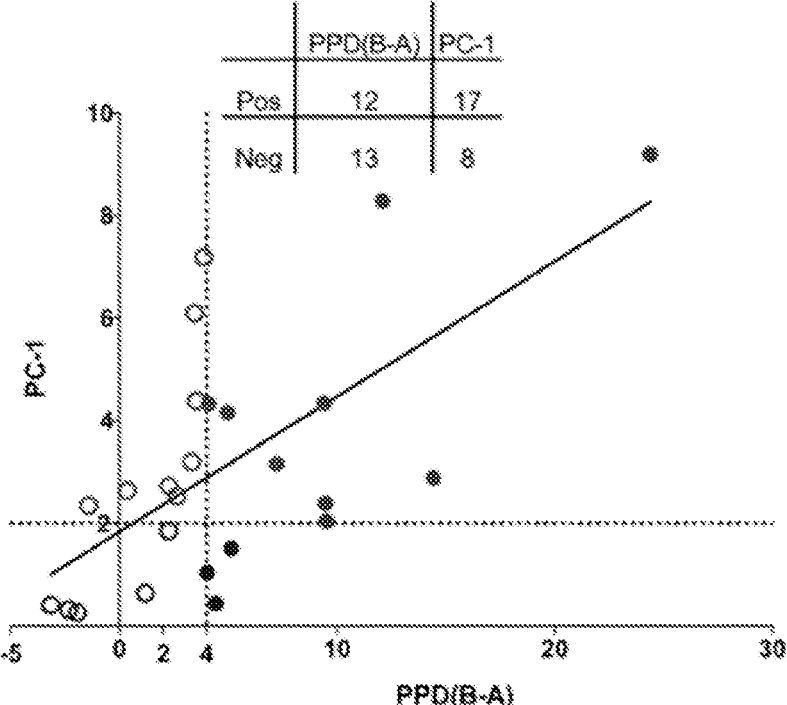
FIG. 7 shows how each of the animals represented in FIG. 5 responded to the SICCT test (PPD(B-A)) and to PC-1. The open circles show SICCT-negative animals, and the closed circles show SICCT-positive animals.

PCL demonstrates superior performance compared with conventional PPD-based assays in naturally infected cattle in an endemic country setting. To assess and compare the performance characteristics of PCL as a defined skin test antigen with routinely used PPDs in crossbred cattle in endemic country settings, we tested PCL and PC-1 alongside PPD-A and PPD-B in a naturally infected herd of Zebu cattle in Ethiopia (n=25). The results showed that PPD-B, PCL and PC-1 identified 22, 19 and 17 animals, respectively, of the 25 animals in this herd as infected (FIG. 5). PCL, PC-1 and PPD-B identified a greater number of infected animals compared to the SICCT, which only correctly classified 12 of 25 animals (FIG. 5). The disappointing performance of the SICCT in this herd is consistent with the observations that a high burden of exposure to environmental mycobacteria, as evidenced by the increase in skin thickness induced by PPD-A (FIG. 5), is a well-known SICCT confounder reducing its sensitivity (15, 31, 32). Indeed, in the herd tested, 10/22 PPD-B positive animals tested SICCT negative due to a stronger response to PPD-A than PPD-B (FIG. 5). Furthermore, of the 13 animals that tested negative in the SICCT (FIG. 6, closed squares+open circles), 9 tested positive to PCL (FIG. 6, closed squares) demonstrating that the majority (69%) of naturally infected animals missed by SICCT were detected by PCL. PCL also matched the number of positives obtained with the high sensitivity interpretation of SICCT (severe interpretation). A similar situation is true for PC-1 (as seen in FIG. 7). Taken together, the suggestion of superior performance of PCL and PC-1 compared to SICCT presented in this study in a high-bTB burden herd with concurrent high levels of sensitization to environmental mycobacteria is encouraging and prioritizes them for further evaluations to accurately define their performance under field conditions.

Figure 9:
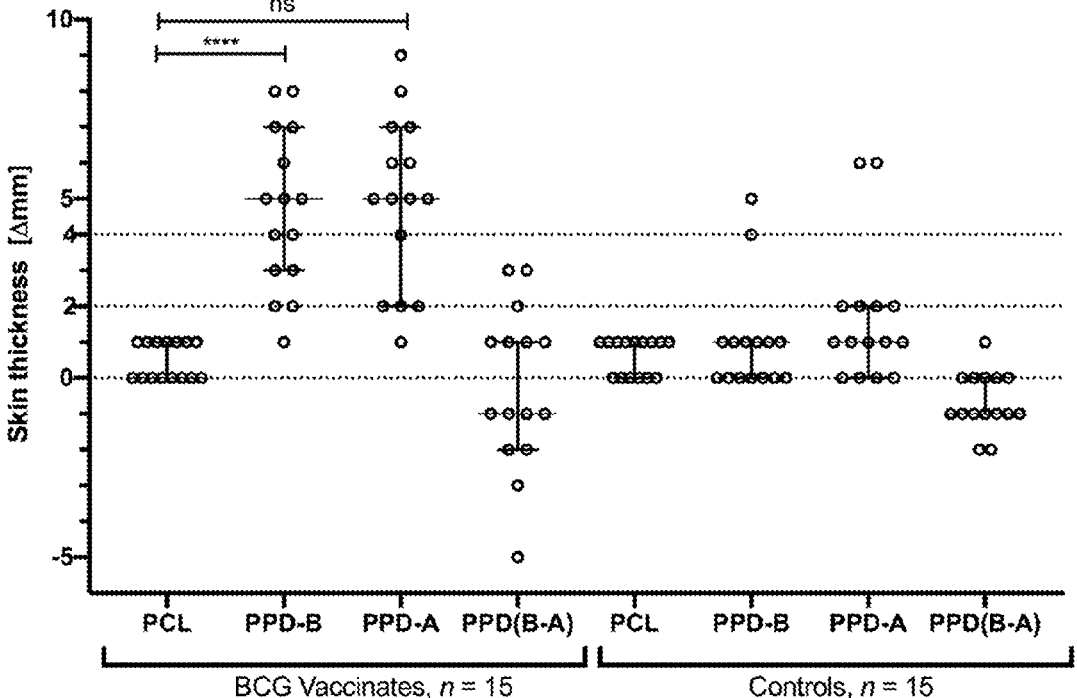
FIG. 9 shows the skin-test performance of PCL compared to PPD-B and PPD-A tested in calves vaccinated with BCG (n=15) and naïve controls (n=15) identified in India. Skin test responses were measured 72 hours post-injection. PPD (B-A) shows the results of a SICCT test, with the raw data for the SICCT test given in the PPD-B and PPD-A columns. Results are expressed as the difference in skin thickness (in millimeters) between pre- and post-skin test readings, with the horizontal line providing the median [±95% confidence interval (CI)]. The statistical difference between the responses was determined using analysis of variance (ANOVA) (****, P<0.0001). The dotted horizontal lines at 2 and 4 mm are the cutoffs used for PCL, and PPD-B and PPD (B-A), respectively. The two control animals that are SIT positive are the same two that show >4 mm PPD-A responses.

PCL provides DIVA capability We next tested specificity of PCL in skin tests in BCG vaccinated calves. Skin test responses to PCL, PPD-A and PPD-B were recorded 6 weeks post-BCG vaccination, the time point with the highest cell-mediated responses. The PCL cocktail induced minimal, if any, increase in skin thickness in both BCG vaccinates and control calves 72 hours post-injection (FIG. 9). In contrast, PPD-B induced a DTH response (of ≥4 mm) in 10/15 (0.67; 95% CI: 0.42, 0.85) of BCG vaccinates and 2/15 (0.13; 95% CI: 0.03, 039) unvaccinated controls that would be considered as reactors per the traditional single intradermal test. However, due to the equally high skin responses to PPD-A observed in BCG vaccinated calves, none of the vaccinated animals were classified as reactors under standard interpretation conditions of the comparative cervical intradermal test (PPD-B minus PPD-A≥4 mm) (FIG. 9). Of note, both the animals in the unvaccinated control group that exhibited ≥4 mm PPD-B stimulated skin induration responses also had a high (≥4 mm) PPD-A response (FIG. 9). This data shows that the PCL cocktail has more consistent results than the PPD (B-A) test, and that the PCL cocktail has DIVA capability. It is noted that no cross-reactivity with environmental mycobacteria was observed in both whole blood IGRA and in the skin test.

Discussion

Comparative genomic, transcriptomic, and proteomic analyses have identified several promising *M. bovis* antigens with DIVA capability including the highly immunogenic proteins ESAT-6, CFP-10 and Rv3615c that are present in *M. bovis* but either absent or not expressed in all BCG vaccine strains (28, 29, 33). Used in combination as defined antigens, these proteins have shown promise in detecting *M. bovis* infected animals and in differentiating them from those vaccinated with BCG in both skin test and in laboratory assays. Synthetic peptide-based DST (defined skin test) reagents for bTB diagnosis have shown promise as an alternative to recombinant proteins (29, 33-35). However, these peptide cocktails were composed of large and complex sets of short overlapping 16-20 mer peptides with technical and cost challenges associated with manufacture and quality assurance of complex peptide mixtures. To address these challenges, the inventors have provided a less complex cocktail of 40-mer long overlapping peptides (PCL) that is equivalent in inducing skin responses in infected animals, whilst maintaining the high specificity in naïve or BCG vaccinated animals.

The inventors mapped the immuno-dominant components within PCL as well as a shorter set of overlapping peptides using ELISPOT assays (FIG. 8). The findings suggest that while most of the PCL peptides were strongly recognized, a smaller subset appeared poorly antigenic for reasons that are not fully understood but may include steric hindrance in fitting of the peptides in the MHC binding groove or inappropriate processing (36, 37). For example, 5 appeared to be poorly recognized in ELISPOT assays, while the short peptide 25, whose sequence is located within 5, was recognized promiscuously (FIG. 8). In contrast, a number of the long peptides, such as 7 and 8 on the C-terminus of CFP-10, elicited a far stronger response than short peptides 29 to 240 that cover the same region of the sequence. These observations highlight the opportunity to optimize and refine the cocktail composition by inclusion of combinations of immuno-dominant long and short peptides that together elicited both broad and promiscuous responses.

Figures 5A, 5B:
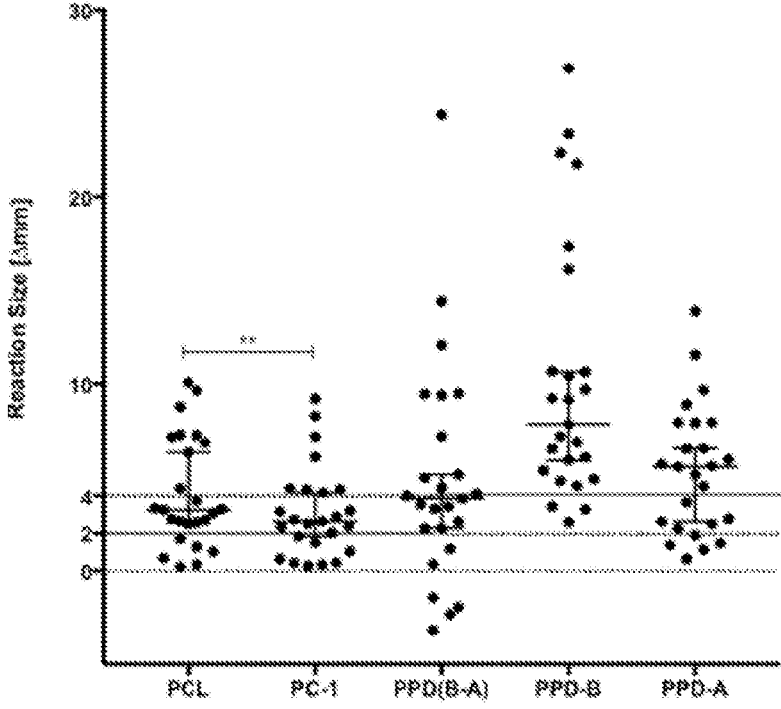
FIG. 5A shows the skin-test performance of a series of reagents tested in naturally infected animals identified in Ethiopia (n=25). PCL and PC-1 are different ESAT6/CFP10/Rv3615c peptide cocktails. PPD(B-A) shows the results of a SICCT test, with the raw data for the SICCT test is given in the PPD-B and PPD-A columns. The horizontal line provides the median (±95% CI). Positivity is defined as >4 mm or PPD(B-A) and PPD-B, and as 2 mm for PCL and PC-1. The statistical difference between PCL and PC-1 responses was determined by using two-tailed t test (**, P<0.01).
FIG. 5B shows the calculations of relative sensitivity of the peptide cocktails, SIT and SICCT of FIG. 5A.

To explore this possibility, a refined combination of peptide antigens was designed (PC-1) and evaluated in vitro and in animal studies. The results showed a similar in vitro IFN-γ response of both PC-1 and PCL in reactor cattle (FIG. 4). Since studies performed under controlled experimental conditions often overestimate diagnostic test performance in comparison with field studies, we next sought to assess and confirm the performance of the peptide cocktails under field conditions in a bTB endemic region. The results show that there is no significant difference in the proportion of animals testing positive to PC-1 and PCL in skin tests (FIG. 5B). Together, these data provide compelling evidence of the potential to reduce the complexity of the peptide cocktail even while further enhancing and optimizing performance characteristics by selecting the optimal combination of dominant long and short peptides for inclusion as a defined skin test (DST) antigen.

To assess performance characteristics in endemic country settings, the relative sensitivity of the PCL and PC-1 peptide cocktails was assessed in a group of 25 naturally infected reactor crossbred cattle in Ethiopia. The results confirm that the relative diagnostic sensitivity of the synthetic peptide cocktails (PCL and PC-1) did not significantly differ from that of the SIT (PPD-B) (FIG. 5B). In contrast, at 48%, the relative sensitivity of the PPD-B-PPD-A response was 40% lower than that observed for PPD-B alone, suggesting that in these animals, the relative sensitivity of the widely used and OIE prescribed SICCT assay for endemic regions was significantly lower than that of the SIT (P=0.005; Fisher exact; two-tailed). While this finding is not altogether surprising given the likely high burden of environmental mycobacteria in Ethiopia and other countries in which bTB remains endemic, it underscores the primary dilemma of tuberculin based skin testing in bTB endemic countries with high or unknown burden of environmental mycobacteria: The use of PPD-B alone as in with the SIT often results in high rates of false positive results due to sensitization with environmental mycobacteria; and conversely, the comparative (SICCT) test has the potential for a high false negative rate due to the masking of the PPD-B responses in animals sensitized with environmental mycobacteria (15, 31). In contrast, by using defined antigens, the skin test diagnostic reagent, or "DST reagent" of the invention has the potential to obviate many of the limitations of traditional tuberculin-based tests, and also provides an opportunity to obtain diagnostic sensitivities equivalent to that of the SIT and specificities equal or exceeding the SICCT all within a single injection site.

Interestingly, the results of this and other studies (29, 35) suggest that use of defined antigens provide considerably lower amplitude of skin reactions in reactor animals (in this study: 8 mm±1.5 with PCL as compared with an average 19.5 mm±3.5 with PPD-B) without compromising sensitivity. Furthermore, since the skin test diagnostic reagent, which may otherwise be referred to as "DST reagent" of the invention obviates the need for administration of PPD-A to improve test specificity, animals that are exposed to environmental mycobacteria that lack or do not express the DST antigens of the invention remain unreactive, providing a considerable technical advantage as well as animal welfare benefits when considering routine surveillance of animals in regions with high exposure to environmental mycobacteria.

REFERENCES

1. E. L. Corbett et al., The growing burden of *tuberculosis*: global trends and interactions with the HIV epidemic. *Archives of internal medicine* 163, 1009-1021 (2003).
2. C. Dye, S. Scheele, P. Dolin, V. Pathania, M. C. Raviglione, Consensus statement. Global burden of *tuberculosis*: estimated incidence, prevalence, and mortality by country. WHO Global Surveillance and Monitoring Project. *Jama* 282, 677-686 (1999).
3. WHO Global TB Report (www.who.int/tb/publications/factsheet_global.pdf). (2018).
4. WHO Zoonotic TB Factsheet (www.who.int/tb/zoonoticTB.pdf).
5. S. Gagneux, Ecology and evolution of *Mycobacterium tuberculosis. Nature Reviews Microbiology* 16, 202 (2018).
6. B. Müller et al., Zoonotic *Mycobacterium bovis*-induced *tuberculosis* in humans. *Emerging infectious diseases* 19, 899-908 (2013).
7. N. H. Smith, R. G. Hewinson, K. Kremer, R. Brosch, S. V. Gordon, Myths and misconceptions: the origin and evolution of *Mycobacterium tuberculosis. Nature Reviews Microbiology* 7, 537 (2009).
8. N. F. Egbe et al., Abattoir-based estimates of mycobacterial infections in Cameroon. *Scientific Reports* 6, 24320 (2016).
9. G. Jiang et al., Pulmonary Tuberculosis Caused by *Mycobacterium bovis* in China. *Scientific Reports* 5, 8538 (2015).
10. C. Thoen, P. LoBue, I. de Kantor, The importance of *Mycobacterium bovis* as a zoonosis. *Veterinary Microbiology* 112, 339-345 (2006).
11. E. Brooks-Pollock, G. O. Roberts, M. J. Keeling, A dynamic model of bovine *tuberculosis* spread and control in Great Britain. *Nature* 511, 228 (2014).
12. A. S. Dean et al., A roadmap for zoonotic *tuberculosis*: a One Health approach to ending *tuberculosis. The Lancet. Infectious diseases* 18, 137-138 (2018).
13. A. L. Olmstead, P. W. Rhode, An Impossible Undertaking: The Eradication of Bovine Tuberculosis in the United States. *The Journal of Economic History* 64, 734-772 (2004).
14. N. H. Smith, R. Clifton-Hadley, Bovine TB: don't get rid of the cat because the mice have gone. *Nature* 456, 700 (2008).
15. R. de la Rua-Domenech et al., Ante mortem diagnosis of *tuberculosis* in cattle: a review of the tuberculin tests, gamma-interferon assay and other ancillary diagnostic techniques. *Research in veterinary science* 81, 190-210 (2006).
16. I. Schiller et al., Bovine *tuberculosis*: a review of current and emerging diagnostic techniques in view of their relevance for disease control and eradication. *Transboundary and emerging diseases* 57, 205-220 (2010).
17. H. Panel on Animal, Welfare, *Scientific Opinion on the use of a gamma interferon test for the diagnosis of bovine tuberculosis*. (2012), vol. 10.
18. P. R. Wood, S. L. Jones, BOVIGAM: an in vitro cellular diagnostic test for bovine *tuberculosis. Tuberculosis (Edinburgh, Scotland)* 81, 147-155 (2001).
19. M. Good, D. Bakker, A. Duignan, D. M. Collins, The History of In Vivo Tuberculin Testing in Bovines: Tuberculosis, a "One Health" Issue. *Frontiers in Veterinary Science* 5, 59 (2018).
20. H. Yang, N. A. Kruh-Garcia, K. M. Dobos, Purified protein derivatives of tuberculin—past, present, and future. *FEMS immunology and medical microbiology* 66, 273-280 (2012).
21. *OIE. Manual of diagnostic Test and Vaccines for Terrestrial Animals. World Organisation for Animal Health* (2009).
22. R. Brosch et al., Genome plasticity of BCG and impact on vaccine efficacy. *Proceedings of the National Academy of Sciences* 104, 5596-5601 (2007).
23. A. Calmette, et al., A Human Strain of Tubercle *Bacillus* Cultivated for 22 Years on Bile Media. *Ann. Inst. Pasteur* 50: 599-603, (1933).

24. W. R. Waters, M. V. Palmer, B. M. Buddle, H. M. Vordermeier, Bovine *tuberculosis* vaccine research: historical perspectives and recent advances. *Vaccine* 30, 2611-2622 (2012).

25. D. B. Young, B. D. Robertson, TB Vaccines: Global Solutions for Global Problems. *Science* 284, 1479 (1999).

26. M. Vordermeier, S. V. Gordon, A. R. Hewinson, Antigen mining to define *Mycobacterium bovis* antigens for the differential diagnosis of vaccinated and infected animals: A VLA perspective. *Transboundary and emerging diseases* 56, 240-247 (2009).

27. H. M. Vordermeier et al., Development of diagnostic reagents to differentiate between *Mycobacterium bovis* BCG vaccination and *M. bovis* infection in cattle. *Clinical and diagnostic laboratory immunology* 6, 675-682 (1999).

28. H. M. Vordermeier, G. J. Jones, B. M. Buddle, R. G. Hewinson, B. Villarreal-Ramos, Bovine Tuberculosis in Cattle: Vaccines, DIVA Tests, and Host Biomarker Discovery. *Annu Rev Anim Biosci* 4, 87-109 (2016).

29. A. O. Whelan et al., Development of a skin test for bovine *tuberculosis* for differentiating infected from vaccinated animals. *Journal of clinical microbiology* 48, 3176-3181 (2010).

30. M. Vordermeier, A. O. Whelan, R. G. Hewinson, Recognition of Mycobacterial Epitopes by T Cells across Mammalian Species and Use of a Program That Predicts Human HLA-DR Binding Peptides To Predict Bovine Epitopes. *Infection and immunity* 71, 1980 (2003).

31. M. Good, A. Duignan, Perspectives on the History of Bovine TB and the Role of Tuberculin in Bovine TB Eradication. *Veterinary Medicine International* 2011, (2011).

32. M. V. Palmer et al., Effects of Different Tuberculin Skin-Testing Regimens on Gamma Interferon and Antibody Responses in Cattle Experimentally Infected with <em> *Mycobacterium bovis*lt;/em>. *Clinical and Vaccine Immunology* 13, 387 (2006).

33. H. M. Vordermeier et al., Use of synthetic peptides derived from the antigens ESAT-6 and CFP-10 for differential diagnosis of bovine *tuberculosis* in cattle. *Clinical and diagnostic laboratory immunology* 8, 571-578 (2001).

34. C. Casal et al., Evaluation of two cocktails containing ESAT-6, CFP-10 and Rv-3615c in the intradermal test and the interferon-γ assay for diagnosis of bovine *tuberculosis*. *Preventive veterinary medicine* 105, 149-154 (2012).

35. G. J. Jones, A. Whelan, D. Clifford, M. Coad, H. M. Vordermeier, Improved skin test for differential diagnosis of bovine *tuberculosis* by the addition of Rv3020c-derived peptides. *Clinical and vaccine immunology: CVI* 19, 620-622 (2012).

36. P. Wang et al., A Systematic Assessment of MHC Class II Peptide Binding Predictions and Evaluation of a Consensus Approach. *PLoS computational biology* 4, e1000048 (2008).

37. M. Wieczorek et al., Major Histocompatibility Complex (MHC) Class I and MHC Class II Proteins: Conformational Plasticity in Antigen Presentation. *Frontiers in immunology* 8, 292-292 (2017).

38. J. Alvarez et al., Evaluation of the sensitivity and specificity of bovine *tuberculosis* diagnostic tests in naturally infected cattle herds using a Bayesian approach. *Vet Microbiol* 155, 38-43 (2012).

39. S. Srinivasan et al., Prevalence of Bovine Tuberculosis in India: A systematic review and meta-analysis. *Transboundary and emerging diseases*, (2018).

40. H. M. Vordermeier et al., Correlation of ESAT-6-specific gamma interferon production with pathology in cattle following *Mycobacterium bovis* BCG vaccination against experimental bovine *tuberculosis*. *Infection and immunity* 70, 3026-3032 (2002).

What is claimed herein is:

1. A skin test diagnostic reagent comprising:
    a 40mer polypeptide consisting of SEQ ID NO: 1;
    a 40mer polypeptide consisting of SEQ ID NO: 3;
    a 40mer polypeptide consisting of SEQ ID NO: 4;
    a 40mer polypeptide consisting of SEQ ID NO: 7;
    a 40mer polypeptide consisting of SEQ ID NO: 8;
    a 40mer polypeptide consisting of SEQ ID NO: 10;
    a 40mer polypeptide consisting of SEQ ID NO: 11; and
    a 40mer polypeptide consisting of SEQ ID NO: 12;
    wherein the reagent elicits a positive result when administered in a skin test to an animal infected with *Mycobacterium bovis* or *Mycobacterium tuberculosis*.

2. The skin test diagnostic reagent according to claim 1, further comprising at least 1, 2, 3 or 4 further different polypeptides, each selected from:
    a 40mer polypeptide consisting of SEQ ID NOs: 2, 5, 6 and 9; and
    a 20mer polypeptide consisting of SEQ ID NO: 38.

3. The skin test diagnostic reagent according to claim 1, comprising each of the 40mer polypeptides consisting of SEQ ID NOs: 1, 2, 3, 4, 5, 6, 7, 8, 9, 10, 11 and 12 and the 20mer polypeptide consisting of SEQ ID NO: 38.

4. The skin test diagnostic reagent according to claim 1, comprising at least 1, 2 or 3 further different polypeptides, each selected from:
    a 20mer polypeptide consisting of SEQ ID NOs: 17, 25, 36 and 39.

5. The skin test diagnostic reagent according to claim 1, comprising each of the 40mer polypeptides having SEQ ID NOs: 1, 3, 4, 7, 8, 10, 11 and 12, and each of the 20mer polypeptides having SEQ ID NOs: 17, 25, 36 and 39.

6. The skin test diagnostic reagent according to claim 1, for use in a method of detecting *Mycobacterium bovis* or *Mycobacterium tuberculosis* infection in an animal.

7. A method of detecting *Mycobacterium bovis* or *Mycobacterium tuberculosis* infection in an animal comprising conducting a skin test on the animal using at least one skin test diagnostic reagent according to claim 1.

8. A diagnostic kit comprising the skin test diagnostic reagent according to claim 1.

9. The diagnostic kit according to claim 8, wherein the diagnostic reagent is able to detect a *Mycobacterium bovis* or *Mycobacterium tuberculosis* infection in a mammal.

10. The diagnostic kit according to claim 9, wherein the diagnostic reagent is able to differentiate between a *Mycobacterium bovis* or *Mycobacterium tuberculosis* infected mammal and a mammal vaccinated against *Mycobacterium bovis* or *Mycobacterium tuberculosis* infection.

11. The diagnostic kit according to claim 8, wherein the diagnostic reagent is in liquid form and included in at least one aliquot of 0.05-0.15 ml containing 1-20 μg of each polypeptide contained in the skin test diagnostic reagent.

* * * * *